US 6,645,248 B2

(12) United States Patent
Casutt

(10) Patent No.: US 6,645,248 B2
(45) Date of Patent: Nov. 11, 2003

(54) ARTIFICIAL INTERVERTEBRAL DISC

(75) Inventor: Simon Casutt, Gossau (CH)

(73) Assignee: Sulzer Orthopedics Ltd., Baar (CH)

(*) Notice: Subject to any disclaimer, the term of this patent is extended or adjusted under 35 U.S.C. 154(b) by 0 days.

(21) Appl. No.: 10/226,524

(22) Filed: Aug. 23, 2002

(65) Prior Publication Data
US 2003/0045939 A1 Mar. 6, 2003

(30) Foreign Application Priority Data
Aug. 24, 2001 (EP) ............................................. 01810828

(51) Int. Cl.$^7$ ................................................. A61F 2/44
(52) U.S. Cl. ........................... 623/17.12; 623/17.14; 623/17.15
(58) Field of Search ..................... 623/17.11, 17.12, 623/17.13, 17.14, 17.15; 606/61

(56) References Cited

U.S. PATENT DOCUMENTS

| 3,867,728 A | * | 2/1975 | Stubstad et al. ................ 3/1 |
| 4,911,718 A | * | 3/1990 | Lee et al. ..................... 623/17 |
| 4,932,969 A | * | 6/1990 | Frey et al. .................... 623/17 |
| 5,002,576 A | * | 3/1991 | Fuhrmann et al. ............ 623/17 |
| 5,370,697 A | * | 12/1994 | Baumgartner ................ 623/17 |
| 5,458,642 A | * | 10/1995 | Beer et al. ................... 623/17 |
| 5,674,294 A | * | 10/1997 | Bainville et al. ............. 623/17 |
| 5,674,296 A | * | 10/1997 | Bryan et al. ................. 623/17 |
| 5,989,291 A | * | 11/1999 | Ralph et al. ................. 623/17 |
| 6,063,121 A | * | 5/2000 | Xavier et al. ................ 623/17 |
| 6,402,785 B1 | * | 6/2002 | Zdeblick et al. ........... 623/17.16 |

FOREIGN PATENT DOCUMENTS

| DE | 43 15 757 C1 | | 11/1994 |
| DE | 20019520 | * | 3/2000 |
| DE | 200 19 520 U | | 3/2001 |
| EP | 0 346 269 A2 | | 12/1989 |
| FR | 2 787 016 A1 | | 6/2000 |
| FR | 2 787 018 A1 | | 6/2000 |
| WO | 00/35385 | * | 6/2000 |

* cited by examiner

Primary Examiner—Bruce Snow
(74) Attorney, Agent, or Firm—Christie, Parke & Hale, LLP

(57) ABSTRACT

The invention relates to an artificial intervertebral disc for implanting between two vertebral bodies (W) comprising two end plates (1, 2) which bound a hollow space (4), which is filled with an elastically and/or plastically deformable nucleus (3), at two opposite sides, with the hollow space (4) being enclosed by a tubular fiber ring (5) such that the end plates (1, 2), together with the fiber ring (5), bound the hollow space (4) and the end plates (1, 2) are in tensile connection with the fiber ring (5). The fiber ring (5) is designed as elastically extensible in the radial and axial directions, with the fiber ring (5) having a larger modulus of elasticity than the nucleus (3) and the nucleus (3) and the fiber ring (5) interacting such that the elastic properties of the artificial intervertebral disc show a non-linear behavior with increasing deformation at least with respect to a compression force (F).

20 Claims, 4 Drawing Sheets

Figure 1:
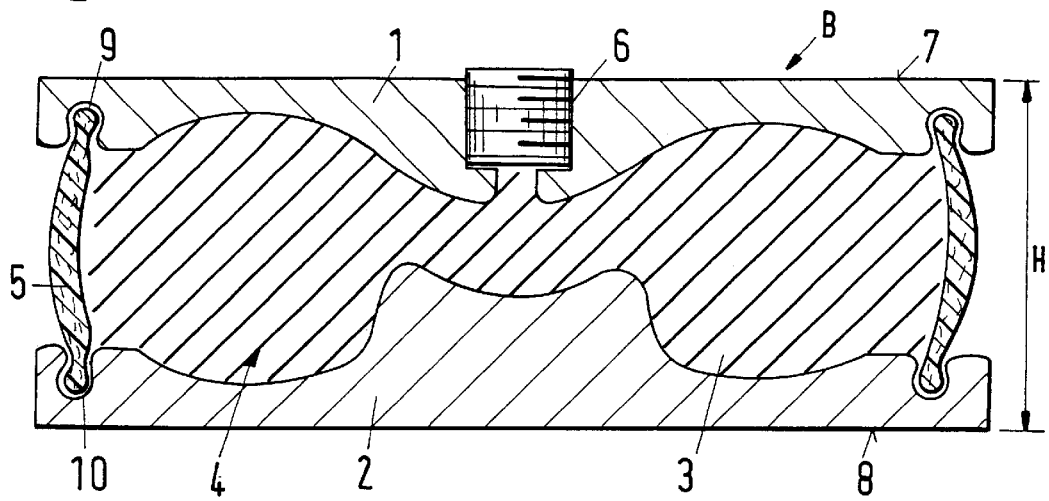

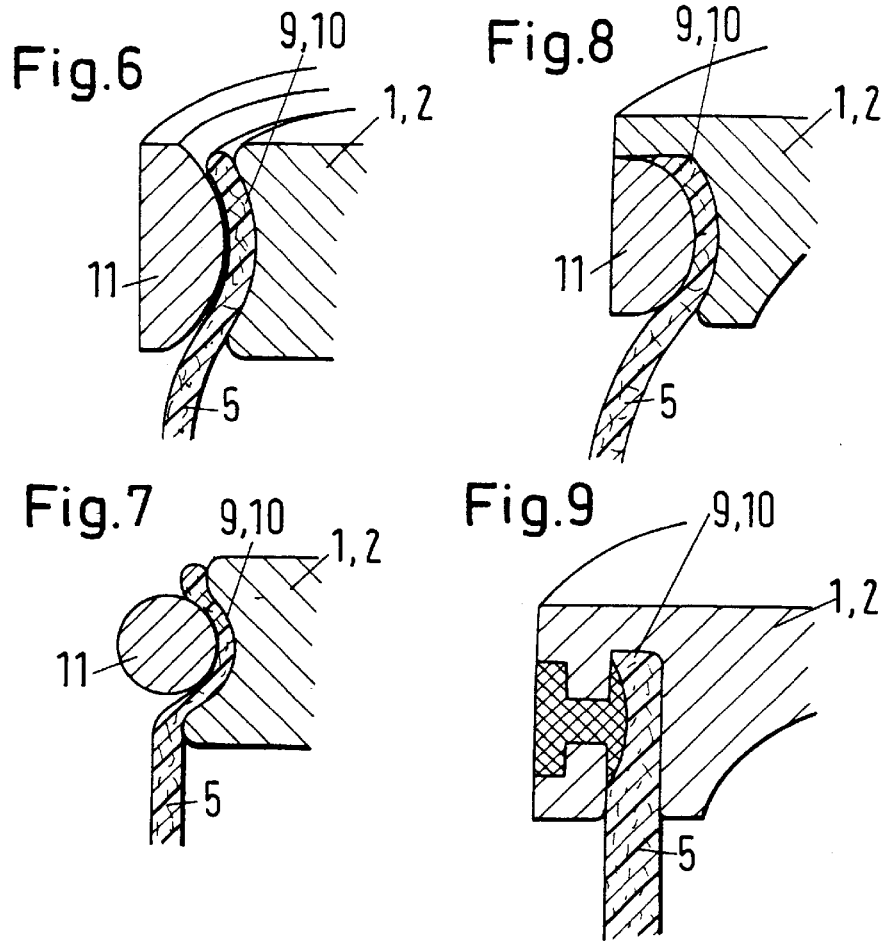
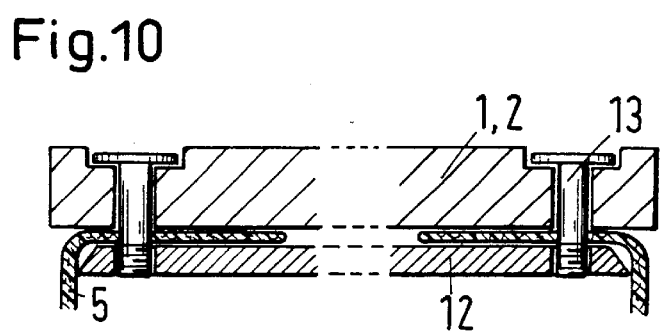
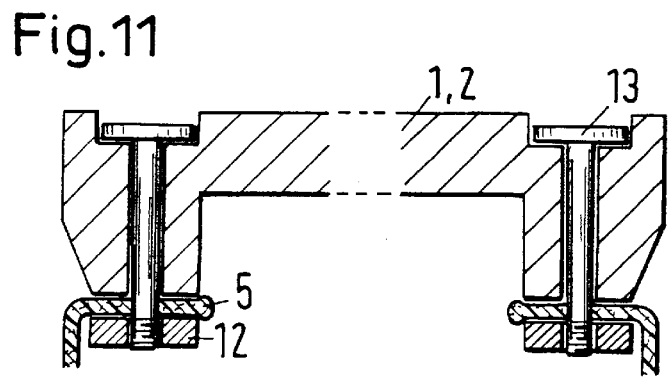

ARTIFICIAL INTERVERTEBRAL DISC

The invention relates to an artificial intervertebral disc in accordance with the preamble of claim 1.

The intervertebral disc takes on a plurality of central functions simultaneously in the vertebral column. It functions as a damper, as a spacer body and also as a joint between the vertebral bodies. The demands to be made on an implant which is intended to serve as a replacement for a natural intervertebral disc in its function as an artificial intervertebral disc are correspondingly complex. For instance, the artificial intervertebral disc must naturally be made up of biocompatible materials and, as a permanent implant, must fulfill its function for the patient for life where possible. In addition to the simple function as a spacer body, the artificial intervertebral disc must in particular be able to effectively cushion the impact forces occurring in the vertebral column so that the vertebrae are not subject to excess stress—however, without noticeably hindering the movability of the vertebrae. A fixed connection must be ensured between the artificial intervertebral disc and the adjoining vertebra in order to suitably lead off the natural stresses of turning, tilting and shearing such as typically occur in the vertebral column.

The highest demands are thus also to be made, in particular on the elastic properties of the artificial intervertebral disc, both as regards its behaviour with respect to torsion stresses, flexural stresses and shear stresses and with respect to pressure stresses. Overall, this means that the mechanical properties of the artificial intervertebral disc have to be reproduced as identically as possible to those of the natural intervertebral disc.

Numerous approaches are known for the replication of the natural properties of an intervertebral disc. For instance, artificial intervertebral discs are known from EP-0 346 269 B1 which consist of two end plates, which are oppositely arranged, are connected via a corrugated tube and are filled with a viscoelastic material. The hitherto unsolved problem of such arrangements, however, also lies in reproducing the suitable, that is the natural, very non-linear, characteristics of an intervertebral disc in the usual stress range for pressure stresses, tensions stresses, shear stresses, bending stresses, flexural stresses and torsion stresses in an artificial intervertebral disc.

It is therefore the object of the invention to propose an artificial intervertebral disc which reproduces the complex, elastic properties of a natural intervertebral disc as exactly as possible.

The artificial intervertebral disc which satisfies this object is characterised by the features of independent claim 1. The dependent claims relate to particularly advantageous embodiments of the invention.

The artificial intervertebral disc of the invention for implantation between two adjacent vertebral bodies comprises two end plates which bound a hollow space, which is filled with an elastically and/or plastically deformable nucleus, at two opposite sides, with the hollow space being enclosed by a tubular fibre ring such that the end plates, together with the fibre ring, bound the hollow space and the end plates are in tensile connection with the fibre ring. The fibre ring is designed as elastically extensible in the radial and axial directions, with the fibre ring having a larger modulus of elasticity than the nucleus. The nucleus and the fibre ring interact such that the elastic properties of the artificial intervertebral disc show a non-linear behaviour with increasing deformation at least with respect to a compression force.

In the artificial intervertebral disc of the invention, two opposite end plates are connected at their peripheries by means of an elastically deformable fibre ring which exerts a constant tensile force on the end plates in the unstressed state such that the nucleus, which is located between the two end plates within the fibre ring, is under pressure bias. An essential disadvantage of known artificial intervertebral discs lies in the fact that under the effect of an elastic deformation either too long a path is stressed until the actual stress region is reached or the starting stiffness already shows values which are too high. A decisive advantage of the artificial intervertebral disc of the invention can therefore be seen in the fact that its elastic behaviour shows a non-linear behaviour at even small deformations at least with respect to compression.

The elastic behaviour of the artificial intervertebral disc of the invention is in this respect determined by the materials encompassing the fibre ring and the nucleus and in particular by the design-determined mechanical coupling of the fibre ring and the nucleus adjoining it, with the specific design of the fibre ring, among other things, being of special importance for the elastic properties of the artificial intervertebral disc. For instance, the mechanical behaviour of the fibre ring with respect to elongation under pressure stress and elongation, for example, as a result of torsional movements, bending movements or transverse displacement movements can already be different due to the type of fabric structure, depending on whether the fibre ring was woven, knitted, braided or manufactured in another manner. In this respect, among other things, the orientation of the fibres, of which the fibre ring is made up, in their slanting position with respect to the direction of the longitudinal axis of the artificial intervertebral disc play a roll for the forces to be transferred between the end plates. A conversion of the different stresses which occur into a compression of the disc can be achieved by the combination of the fibre ring and the nucleus and by an opposite slanting position of the fibres relative to the direction of the longitudinal axis of the artificial intervertebral disc.

The nucleus is filled as a fluid into the artificial intervertebral disc under pressure through a closable opening in one of the cover plates. A fluid in its widest sense can also be understood, for example, as a dried gel present in granular or powder form or as a substance of comparable consistence, with the fluid solidifying after a certain period of time into an elastic or at least partly plastic body or permanently maintaining its fluid properties as a more or less viscous liquid. It is decisive for the function of the artificial intervertebral disc that the nucleus formed in this way preferably completely fills up the hollow space which the cover plates form with the fibre ring, on the one hand, and has permanent low incompressibility and is under pressure bias, on the other hand. It is thereby ensured that the nucleus is in direct active connection with the fibre ring and can so act as a force transformer. If the artificial intervertebral disc built up in this manner is exposed, for example, to a pressure stress, the nucleus must escape in a partly radially outward manner under the compression effect and thereby expands the fibre ring, whereby the forces from the pressure stress are at least partly transformed into the fibre ring.

Since the nucleus is already under a certain pressure bias, which can be set as desired within wide limits by the filling pressure, in the unstressed state via the fibre ring, the starting stiffness can already be adjusted solely by the filling pressure of the fluid. The possibility thus exists to adapt the elastic properties to the individual needs of a patient while observing a pre-determined geometry for the artificial intervertebral disc and without changing or replacing the materials which make up the artificial intervertebral disc. In this manner, the non-linear stress characteristics can be matched, for example, to the body weight of the patient. Furthermore, the elastic behaviour can naturally be influenced both by the selection of the materials of which the nucleus or the fibre ring are respectively made up and by the specific design of the geometry of the components making up the artificial intervertebral disc.

The materials which make up the fibre ring include biocompatible plastics to the extent that they come into contact with body tissue. The fibre ring itself can be permeable for the body's own liquids, but must be completely impermeable for the nucleus. The end plates can be made of a metal, for example of robust titanium, or of a robust titanium alloy, which is plastically deformable for the anchoring of the fibre tube. The outer surfaces of the end plates can have zones with a metal web which facilitate the growing in of bone material and thus the intergrowth of the adjoining vertebrae with the outer surfaces of the end plates. An improvement of the anchoring between the end plate and the vertebra with respect to lateral forces can be achieved by one or more projecting ribs which extend, for example, from ventral to dorsal. An additional toothed arrangement at the outer edge of the end plate, which—like the projecting rib—does not have to be present mandatorily, can likewise substantially improve the connection between the end plate and the vertebra with respect to shear stresses. In this respect, the end plate does not necessarily have to be made up of metal, but suitable biocompatible plastics can, for example, also be considered as materials for the composition of the end plate.

Figure 2:
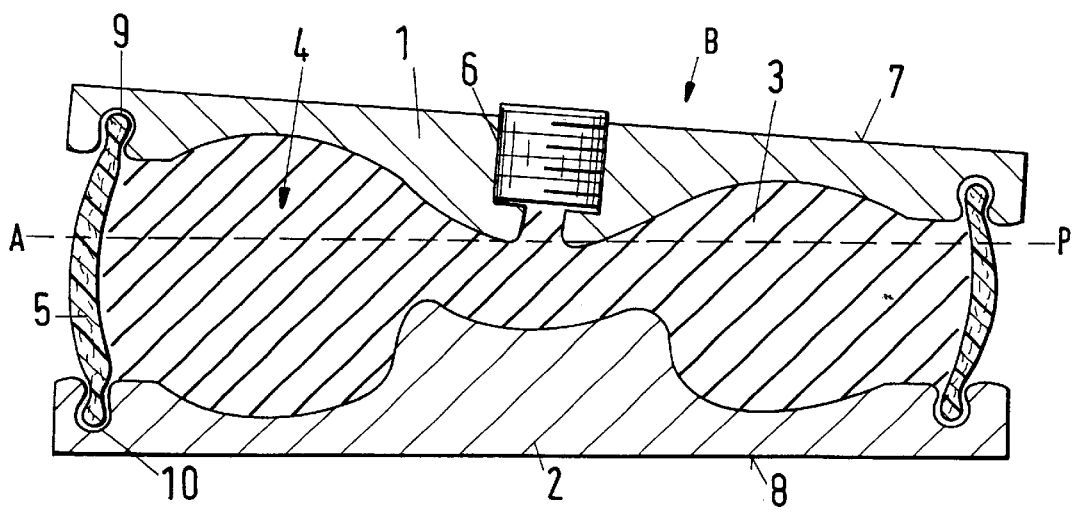
Figure 3:
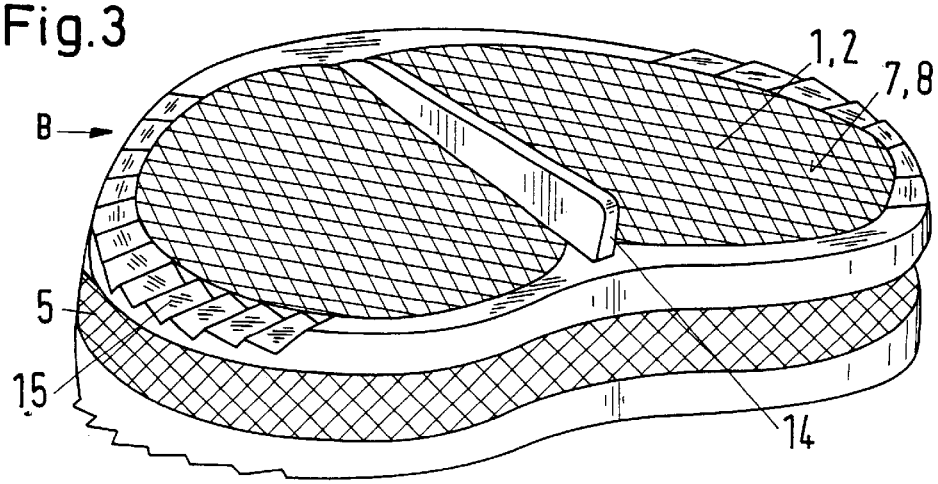
Figure 4:
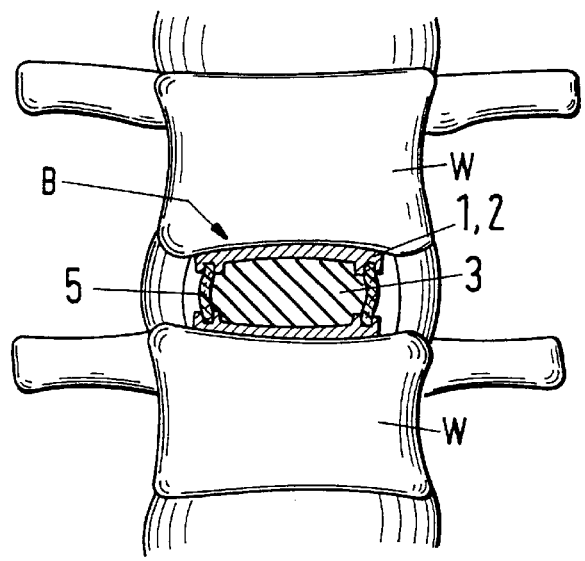
Figure 5:
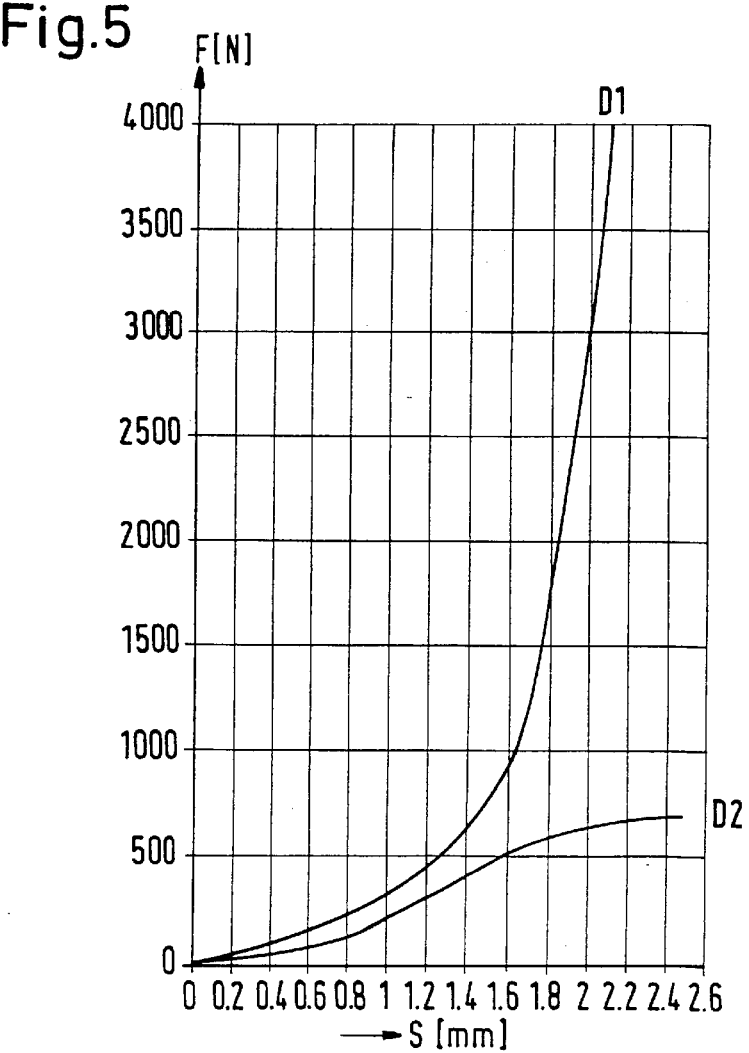
Figure 12:
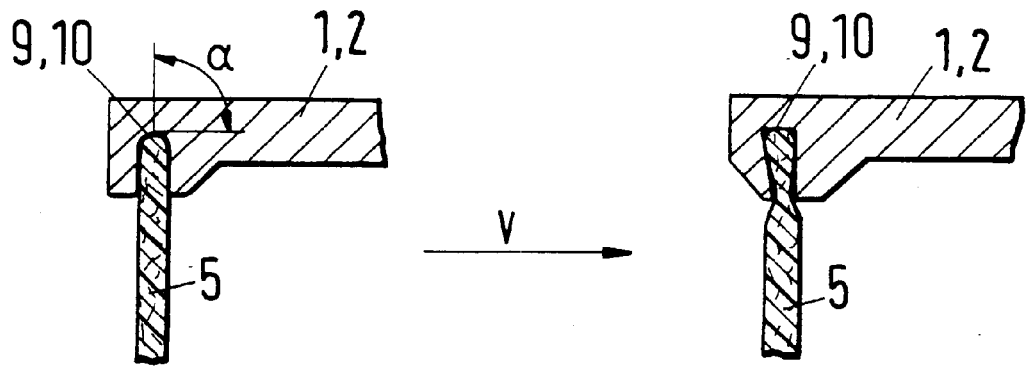
Figure 13:
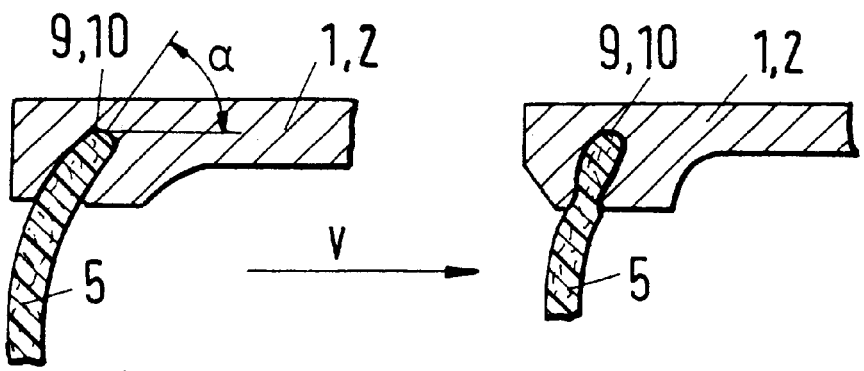
Figure 14:
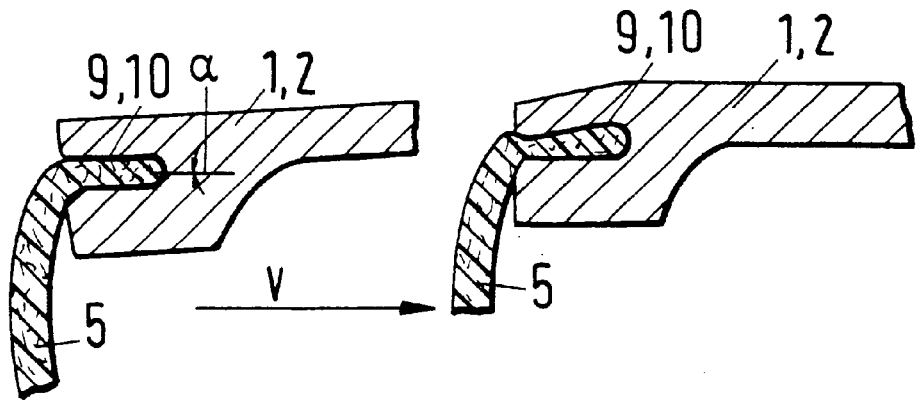

The invention is explained in more detail in the following with reference to preferred embodiments and to the drawing. There are shown:

FIG. 1 schematically, a longitudinal section through an artificial intervertebral disc of the invention having end plates standing parallel to one another;

FIG. 2 a further embodiment analogue to FIG. 1 having end plates which are at an acute angle to one another;

FIG. 3 schematically, a view of a further artificial intervertebral disc;

FIG. 4 an artificial intervertebral disc of the invention inserted between two adjacent vertebral bodies;

FIG. 5 schematically, a force—path diagram of the elastic behaviour of an artificial intervertebral disc of the invention in comparison with a known elastomer prosthesis;

FIG. 6 schematically, an embodiment for the connection of a fibre ring to an end plate by means of an annular clamping element;

FIG. 7 schematically, a second variant of an embodiment in accordance with FIG. 6;

FIG. 8 schematically, a third variant of an embodiment in accordance with FIG. 6, with the fibre ring being additionally adhesively bonded or welded;

FIG. 9 schematically, an embodiment for the connection of the fibre ring to an end plate, with the fibre ring being adhesively bonded, welded or having a plastic injection moulded on;

FIG. 10 schematically, an embodiment for the connection of the fibre ring to an end plate, with the fibre ring being fixed by a holding element;

FIG. 11 schematically, a further embodiment in accordance with FIG. 10;

FIG. 12 schematically, an embodiment for the connection of the fibre ring to an end plate, with the fibre ring being cold pressed in a groove;

FIG. 13 schematically, a second embodiment in accordance with FIG. 12;

FIG. 14 schematically, a third embodiment in accordance with FIG. 12.

The invention is explained in the following with reference to preferred embodiments. The artificial intervertebral disc B of the invention for implanting between two vertebral bodies W comprises two end plates 1, 2 which bound on two opposite sides a hollow space 4 completely filled with an elastically and/or plastically deformable nucleus 3, with the hollow space 4 being surrounded by a tubular fibre ring 5 such that the end plates 1, 2 bound the hollow space 4 together with the fibre ring 5. The end plates 1, 2 are in tensile connection with the fibre ring 5, with the fibre ring 5 being designed in an elastically extensible manner in the radial and the axial directions and with the fibre ring 5 having a larger modulus of elasticity than the nucleus 3. The nucleus 3 and the fibre ring 5 interact such that the elastic properties of the artificial intervertebral disc show a non-linear behaviour with increasing deformation at least with respect to a compression force F.

FIG. 1 shows a preferred embodiment of an artificial intervertebral disc B of the invention in a schematic illustration. A nucleus 3 is tensioned between the end plates 1, 2 by means of the fibre ring 5. The end plates 1, 2 are designed such that the largest possible contact surface is present with respect to the vertebral bodies W in order to keep the surface pressure as low as possible and to prevent penetration of the prosthesis into the vertebral body. The build height H of the artificial intervertebral disc can either be constant or, as shown in FIG. 2, be reducing, for example, from anterior A to posterior P, with a variation of the build height H of the artificial intervertebral disc B also being achieved in that the fibre ring 5 has a constant height over its whole circumference which, however, varies the thickness of the end plates 1, 2 correspondingly. The primary anchoring of the artificial intervertebral disc B to the vertebral body W takes place-via a suitable preparation of the end plates 1, 2 so that a form locked connection is ensured between the end plate 1, 2 and the vertebral body W. This form lock is carried out in accordance with FIG. 3 via a toothed arrangement 15 and/or a projecting rib 14, with an anchoring primarily being effected in the region of the cortical borders since the highest forces can be transferred there. The secondary anchoring of the vertebral bodies W to the end plates 1, 2 is achieved in that the outwardly directed surfaces 7, 8 of the end plates 1, 2 are formed as anchoring platforms such that a permanent intergrowth of the adjoining vertebral bodies W with the outwardly directed surfaces 7, 8 of the end plates 1, 2 is made possible. Specifically, the anchoring platforms can, for example, be designed with grid layers of titanium or of titanium alloys as a "Mesh" or in the form of other net-like or porous structures of titanium or titanium alloys with the largest possible contact surfaces in order to ensure a permanent growing in of the vertebral bodies W at the artificial intervertebral disc B. The end plate 1, 2 itself can be made of a surgical steel or of a plastic such as a high performance polymer such as polyether ether ketone (PEEK), PEEK carbon or polyimide. Titanium or titanium alloys are preferably used which are known for their exceptional bone compatibility and the excellent growing behaviour of bone material at them and which—to the extent that they have good cold reshaping properties—allow a simple and reliable anchoring of the fibre ring 5 at the end plates 1, 2. Moreover, the connection of the anchoring platform to the grid layers made of titanium or titanium alloys can take place by welding.

The nucleus preferably fills up the whole hollow space 4 which is formed by the end plates 1, 2 and the fibre ring 5. The core materials which can be considered for the nucleus 3 should be substantially incompressible, have a modulus of elasticity whose value is less than 100 MPa and be biocompatible in the form used. The core materials which come into question for the nucleus 3 are, for example, hydrogels, plastics based on silicone, polycarbourethane (PCU) or other suitable elastic or plastic plastics or rubber materials. The core material which forms the nucleus is preferably introduced into the hollow space 4 of the artificial intervertebral disc in a liquid form, said artificial intervertebral disc having a closable opening 6 in one of the end plates 1, 2 for this purpose. After the filling of the core material, this can solidify in dependence on the material into, for example, an elastically and/or plastically deformable nucleus 3 and cure, for example, by polymerisation or in another manner. It is naturally also conceivable for the nucleus to keep a high plastic deformability permanently or even to maintain a more or less liquid-like consistence. The filling of the hollow space 4 preferably does not take place intraoperationally; however, this is generally likewise possible. Depending on the desired characteristic for the elastic behaviour of the artificial intervertebral disc B, the core material is poured in with the corresponding pressure and the fibre ring 5 is thus put under a certain bias.

The fibre ring 5 forms one of the technological core elements of the artificial intervertebral disc B. In cooperation with the nucleus 3, it gives the artificial intervertebral disc B the elastic characteristic for all kinds of stress. The fibre ring 5 consist of high-tenacity fibres with a high modulus of elasticity. Materials such as polyethylene terephthalate (PET), but also plastics such as polyamide, polyimide, carbon fibres or, for example, polyether etherketone (PEEK), are possible as preferred materials. The fibre ring 5 is in this respect preferably braided, woven or knitted or manufactured in another manner in one or more layers, with the individual layers being able to have the same or different braiding angles. In this respect, completely different manufacturing processes are possible. For example, flat bands can first be braided which are then sewed to form rings or are, for example, welded ultrasonically. A marginal zone of the fibre ring 5 can easily be braided more thickly in the braiding process, whereby the fibre ring 5 can be better anchored in the end plate 1, 2, for example in a groove 9, 10. A further variant consists of braiding tubes therein which can be sewed to form rings or, for example, welded ultrasonically. Fibres or bands, for example made of polyethylene terephthalate (PET) or titanium, of a titanium alloy or of another suitable materials can be inserted into the marginal zones of the rings, whereby a thickening of the marginal zone is achieved which is suitable for the securing of the fibre ring 5 to the end plate 1, 2, for example in the groove 9, 10. A further variant for the manufacturing of the fibre ring 5 consists of the braiding of an endless tube having a diameter required for the fibre ring 5. The fibre ring 5 is separated, for example thermally, by means of ultrasound or in another manner, from this tube, which can likewise naturally consist of one or more layers, whereby any desired heights can be realised for the fibre ring 5. A marginal zone can be thermally melted and shaped in the separation region during the separation process such that an optimum clamping geometry results so that the fibre ring 5 can be securely anchored in the end plate 1, 2, for example in the groove 9, 10, with it having to be ensured in every case that it does not occur, even under very high pressures such as can act on the artificial intervertebral disc B as an implant in a human vertebral column, that the nucleus 3 or a part thereof can exit through the fibre ring 5 or in another manner. High demands are therefore set on the manufacturing of the fibre ring 5. It must, among other things, be worked so tightly that the nucleus 3 or parts thereof cannot penetrate the fibre ring 5. For this purpose, the fibre ring 5 can, for example, additionally have a sealing layer. On the other hand, it can be of advantage that the hollow space 4 can exchange body liquid with the surroundings. This is in particular of advantage if hydrogels are for example used as the materials for the nucleus 3. Hydrogels have the property that as the degree of hydration increases or decreases, they can show highly corresponding volume changes, with the relationship generally being able to made that hydrogels can highly increase their volume by swelling as the degree of hydration increases and in this condition have a relatively low modulus of elasticity and are therefore unsuitable for applications without a spatial boundary. Since the spatial limitation of the hollow space 4 is ensured by the fibre ring 5 and the end plates 1, 2 with the artificial intervertebral disc B of the invention, hydrogels with a high degree of hydration can also be considered as the material for the nucleus 3. In the artificial intervertebral disc B of the invention, the effect of the hydration of the hydrogel can be utilised in a particularly advantageous manner. If the fibre ring 5 is designed such that it is completely impermeable for the nucleus 3, but permeable for certain body liquids such as water, the volume effect, that is the swelling of the nucleus 3, which consists of a hydrogel, can be utilised by hydration. The artificial intervertebral disc B can namely then be introduced into the vertebral column in a dehydrated state with a highly reduced introduction height, which substantially facilitates an implantation, as a replacement for a removed natural intervertebral disc and still have the shown non-linear behaviour later. Body liquids such as water, which can penetrate the fibre ring 5, increases the volume of the nucleus 3 after the implantation by increasing hydration, said nucleus ultimately reaching an intended end pressure with a predetermined end volume after a certain time.

The decisive factor for the mechanical behaviour of the artificial intervertebral disc B of the invention is its highly non-linear elastic behaviour, for example under a compression force F, with the pressure characteristic being based on an interplay of the nucleus 3 with the fibre ring 5. FIG. 5 shows by way of example a force—path diagram D1 of the elastic behaviour of an artificial intervertebral disc B of the invention in comparison with a typical force—path diagram D2 of a known elastomer prosthesis which does not comprise a fibre ring mechanically coupled to a nucleus.

If the artificial intervertebral disc of the invention is compressed only a little, that is by a path S of much less than approximately 0.5 mm, by a compression force F, which acts, for example, perpendicular to the surfaces 7, 8 of the end plates 1, 2, the modulus of elasticity of the nucleus 3 substantially influences the stress characteristic. In this region, the force—path diagrams D1 and D2 still extend substantially parallel. As the compression path S increases, the fibres of the fibre ring 5 are stretched and the fibre ring 5 bellows out slightly due to the volume shifting of the nucleus 3. Since the nucleus 3 has low compressibility, as the compression force F increases, said nucleus transforms the pressure forces acting on the artificial intervertebral disc B into the fibre ring 5 and induces tensile forces into the fibres of the fibre ring 5. The modulus of elasticity of the fibre ring 5 thus determines the stress characteristic as the compression progresses in an increasing degree, said stress characteristic, as shown impressively by the curve D1, beginning to rise very progressively. The curve D2, in contrast, demonstrates that the elastic behaviour of the known elastomer prosthesis does not show any progressively increasing behaviour. With a compression path which is well over 1 mm, the force—path diagram D2 even shows a degressive behaviour, which is due to unwanted bellowing out of the elastomer core under increasing pressure stress. With the artificial intervertebral disc B of the invention, however, the fibres of the fibre ring 5 surrounding the nucleus 3 can better and better absorb the forces which occur as the bellowing out increases and the geometrical translation resulting therefrom additionally amplifies the progressive increase of the force-path curve D1. As a result, the stress characteristic of the artificial intervertebral disc B can be significantly influenced via the setup of the fibre ring.

It is a particular characteristic of the force-path diagram in FIG. 5 that, analogue to the behaviour of a natural intervertebral disc, the starting increase of the curve already shows a slightly progressive behaviour. This means that the artificial intervertebral disc B of the invention already shows a certain increase in the starting stiffness which is different to zero at any desired small compression force F and thus at any desired small stresses, with stiffness (or starting stiffness) of the artificial intervertebral disc at a compression force F being understood as the corresponding increase in the curve D1 or D2 in the force-path diagram with a deformation path S which is associated with the corresponding compression force F. The intervertebral disc of the invention thus shows a preferred stiffness between 2000 N/mm and 20,000; N/mm at a compression force F of 3000 N and a stiffness whose value is lower than 500 N/mm under a deformation S of approximately 0.4 mm.

Since the non-linear properties of the artificial intervertebral disc B, which shows these with respect to a compression force F, are also transformed by the interplay of the fibre ring 5 and a nucleus 3 into the elastic behaviour with respect to torsion stress, flexural stress and shear stress, the artificial intervertebral disc B shows with respect to these kinds of strain both a certain increase in the starting stiffness and a further progressive increase of the stiffness associated with the corresponding kind of strain even with corresponding deflections from the unstressed state which can be as small as desired. Since the said increase in the starting stiffness is achieved in that the nucleus 3 is under a certain pressure bias via the fibre ring 5 in the unstrained state, the possibility arises of matching the elastic properties to the individual needs of a patient while maintaining a pre-determined geometry for the artificial intervertebral disc B and without changing or replacing the materials making up the artificial intervertebral disc B. In this way, the non-linear strain characteristic and thus the stiffness and its change as the compression force F increases can simply be matched, for example to the body weight of the patient, by a suitable selection of the pressure bias.

The requirement for a good functioning of the artificial intervertebral disc B of the invention is a perfect anchoring of the fibre ring 5 in the end plate 1, 2. A groove 9, 10 in the end plate 1, 2 is shown schematically in FIGS. 6 to 9 and in FIGS. 12 to 14, in which the fibre ring 5 is secured. The kind of securing depends, among other things, on the material of the end plate 1, 2. For instance, the fibre ring 5 can, as shown in FIGS. 6, 7, be fixed to the end plate 1, 2, which is made of metal or of plastic, in the groove 9, 10 by an annular clamping element 11 or be additionally (see FIGS. 8, 9) adhesively bonded in the groove 9, 10. With the end plate 1, 2 of plastic, thermal welding in the groove 9, 10 or at a surface of the end plate 1, 2 is also possible as an alternative to adhesive bonding. With a metallic end plate 1, 2, the fibre ring 5 can be pressed in the groove 9, 10 by cold shaping V. In this respect, the groove 9, 10 can, as shown in FIGS. 12 to 14, be inclined at an angle a against the surface of the end plate 1, 2, with an angle α being selected which lies between 0 degrees (FIG. 14) and 90 degrees (FIG. 12), preferably however in the vicinity of 60 degrees. As a further variant for the securing of the fibre ring 5 to the end plate 1, 2, a fixing by means of an additional holding element 12 is also feasible, that can be made, for example, as a plate (FIG. 10) or as a ring (FIG. 11) and that is preferably secured to the end plate 1, 2 by means of a screw connection 13.

An artificial intervertebral disc B is provided by the invention which for a plurality of reasons is very well suited as an implant and thus as a replacement for a natural intervertebral disc. In its embodiment as a one-part implant, which is made up of only a few components, the artificial intervertebral disc of the invention can be introduced in a simple manner into the human spinal column. It can be supplied prefabricated and sterilised for a corresponding surgical procedure so that complex techniques for the putting together of single parts during a surgical procedure inside the human body or between two vertebral bodies W become superfluous. The distraction of the vertebral bodies W for the introduction of an intervertebral disc prosthesis is a task which generally represents a substantial problem due to the tight space relationships. If, for example, a dehydrated hydrogel is used as the core material for the nucleus 3, the artificial intervertebral disc B has a build height H at the time of introduction into the spinal column which is up to 50% lower in the dehydrated state than in the fully hydrated state. The problems in connection with the distraction are thereby substantially reduced. Due to the special design of the fibre ring 5, to the interaction of the nucleus 3 and the fibre ring 5 and to a suitable choice of the materials, the elastic behaviour of the artificial intervertebral disc B is given a typically nonlinear characteristic with respect to all relevant kinds of strain which almost identically reproduces that of a natural intervertebral disc. Due to the design, the nucleus 3 acts as a force transformer which transforms the strains occurring in the fibre ring 5, whereby the artificial intervertebral disc B receives a realistic elastic characteristic.

What is claimed is:

1. An artificial intervertebral disc for implanting between two vertebral bodies (W) comprising two end plates (1, 2) which bound a hollow space (4), which is filled with an elastically and/or plastically deformable nucleus (3), at two opposite sides, the hollow space (4) comprising an inner region and an outer region surrounding the inner region, the outer region being bounded by opposing faces of the end plates, and the inner region being bounded by a concave bearing face of the one end plate and an opposing convex counterface of the other end plate, the distance between the concave bearing face of the one end plate and the opposing convex counterface of the other end plate in the inner region being smaller than the distance between the opposing faces of the end plates in the outer region, with the hollow space (4) being enclosed by a tubular fibre ring (5) such that the end plates (1, 2), together with the fibre ring (5), bound the hollow space (4) and the end plates (1, 2) are in tensile connection with the fibre ring (5), wherein the fibre ring (5) is designed as elastically extensible in the radial and axial directions, with the fibre ring (5) having a larger modulus of elasticity than the nucleus (3) and the nucleus (3) and the fibre ring (5) interacting such that the elastic properties of the artificial intervertebral disc show a non-linear behaviour with increasing deformation at least with respect to a compression force (F).

2. An artificial intervertebral disc in accordance with claim 1, in which the nucleus (3) is made up of a material whose modulus of elasticity has a value lower than 100 MPa.

3. An artificial intervertebral disc in accordance with claim 1, in which the value for the stiffness of the artificial intervertebral disc lies in a range between 2000 N/mm and 20,000 N/mm when the intervertebral disc is subject to a compression force (F) below 3000 N.

4. An artificial intervertebral disc in accordance with claim 1, in which the fibre ring (5) consists of a fabric, knitted fabric or braided fabric and comprises one or more layers.

5. An artificial intervertebral disc in accordance with claim 1, in which the materials making up the fibre ring (5) comprise one or more plastics such as polyamide, polyimide, carbon fibres, polyether etherketone (PEEK), or polyethylene terephthalate (PET).

6. An artificial intervertebral disc in accordance with claim 1, in which the nucleus (3) is selected from the group consisting of a hydrogel; an elastic plastic based on silicone; another elastic plastic; a hydrogel and an elastic plastic based on silicone; a hydrogel and another elastic plastic; an elastic plastic based on silicone and another elastic plastic; and a hydrogel, an elastic plastic based on silicone, and another elastic plastic.

7. An artificial intervertebral disc in accordance with claim 1, in which the hollow space (6) is accessible by a closable opening (6) in an end plate (1, 2).

8. An artificial intervertebral disc in accordance with claim 1, in which a build height (H) is either constant or reduces from anterior (A) to posterior (P).

9. An artificial intervertebral disc in accordance with claim 1, in which the end plates (1, 2) consist of a metal, of titanium, of a titanium alloy or of plastic.

10. An artificial intervertebral disc in accordance with claim 1, in which the end plates (1, 2) are made as anchoring platforms in order to achieve an intergrowth of the adjoining vertebral bodies (W) with the outwardly directed surfaces (7, 8) of the end plates (1, 2).

11. An artificial intervertebral disc in accordance with claim 10, at which the fibre ring (5) is adhesively bonded or welded at one of the grooves (9, 10) for connection to one of the end plates (1, 2).

12. An artificial intervertebral disc in accordance with claim 1, in which one of the end plates (1, 2) has a groove (9, 10) extending in the peripheral direction in order to accept the fibre ring (5).

13. An artificial intervertebral disc in accordance with claim 12, at which the fibre ring (5) is pressed in one of the grooves (9, 10) by cold shaping for connection to one of the end plates (1, 2).

14. An artificial intervertebral disc in accordance with claim 12, at which the fibre ring (5) is fixed in one of the grooves (9, 10) by an annular clamping element (11) for connection to one of the end plates (1, 2).

15. An artificial intervertebral disc in accordance with claim 12, at which the fibre ring (5) is injection moulded with plastic in an annular manner in one of the grooves (9, 10) of the end plates (1, 2) for connection to one of the end plates (1, 2).

16. An artificial intervertebral disc in accordance with claim 1, at which the fibre ring (5) is fixed by a holding element (12) for connection to one of the end plates (1, 2).

17. An artificial intervertebral disc in accordance with claim 16, in which the holding element is a screw connection (13).

18. An artificial intervertebral disc in accordance with claim 1, at which the fibre ring (5) is injection moulded with plastic at one of the surfaces (7, 8) for connection to one of the end plates (1, 2).

19. An artificial intervertebral disc in accordance with claim 1, in which the end plates (1, 2) have a projecting central rib (14), which extends along the end plates (1, 2).

20. An artificial intervertebral disc in accordance with claim 1, in which the end plates (1, 2) have a toothed arrangement (15) directed towards an outer edge of a vertebral body (W) so that an intergrowth of bone material between the toothed arrangement (15) and the vertebral body (W) allows for the transfer of torsion and flexion forces.

* * * * *